United States Patent
Glaug et al.

[11] Patent Number: 5,399,175
[45] Date of Patent: Mar. 21, 1995

[54] ABSORBENT STRUCTURE HAVING MULTIPLE CANALS

[75] Inventors: Frank S. Glaug, Spotswood; William B. Mattingly, III, East Brunswick, both of N.J.

[73] Assignee: McNeil-PPC, Inc., Milltown, N.J.

[21] Appl. No.: 95,038

[22] Filed: Jul. 20, 1993

Related U.S. Application Data

[60] Continuation of Ser. No. 916,921, Jul. 20, 1992, abandoned, which is a division of Ser. No. 659,200, Feb. 21, 1991, Pat. No. 5,151,091, which is a continuation of Ser. No. 247,820, Oct. 24, 1988, abandoned.

[51] Int. Cl.⁶ .................... A61F 13/15; A61F 13/20
[52] U.S. Cl. .................... 604/385.1; 604/358; 604/368; 604/378; 604/379; 604/381; 604/382
[58] Field of Search .............. 604/358, 368–369, 604/378–385.1

[56] References Cited

U.S. PATENT DOCUMENTS

| | | | |
|---|---|---|---|
| 75,036 | 3/1868 | Manheim | 604/397 |
| 3,071,138 | 1/1963 | Garcia | 604/397 |
| 3,903,890 | 9/1975 | Mesek et al. | 604/369 |
| 3,954,107 | 5/1976 | Chesky et al. | 604/370 |
| 3,993,820 | 11/1976 | Repke | 604/380 |
| 4,015,604 | 4/1977 | Csillag | 604/382 |
| 4,213,459 | 7/1980 | Sigl et al. | 604/380 |
| 4,217,901 | 8/1980 | Bradstreet et al. | 604/368 |
| 4,324,246 | 4/1982 | Mullane et al. | 604/371 |
| 4,360,022 | 11/1982 | Usami et al. | 604/378 |
| 4,589,876 | 5/1986 | Van Tilburg | 605/385.1 |
| 4,676,786 | 6/1987 | Nishino | 604/378 |
| 4,935,021 | 6/1990 | Huffman et al. | 604/385.1 |
| 4,936,839 | 6/1990 | Molee et al. | 604/378 |
| 5,151,091 | 9/1992 | Glaug et al. | 604/385.1 |

FOREIGN PATENT DOCUMENTS 0391727 10/1990 European Pat. Off. ............ 604/378

*Primary Examiner*—Randall L. Green
*Assistant Examiner*—P. Zuttarelli

[57] ABSTRACT

An absorbent structure for absorbing body fluid is provided having means to direct body fluid along the longitudinal axis of the product and to substantially limit side failure. Two or more longitudinal chambers of absorbent material are provided which are separated by fluid repellent walls. These walls act to guide flow generally along the longitudinal axis of the product.

23 Claims, 3 Drawing Sheets

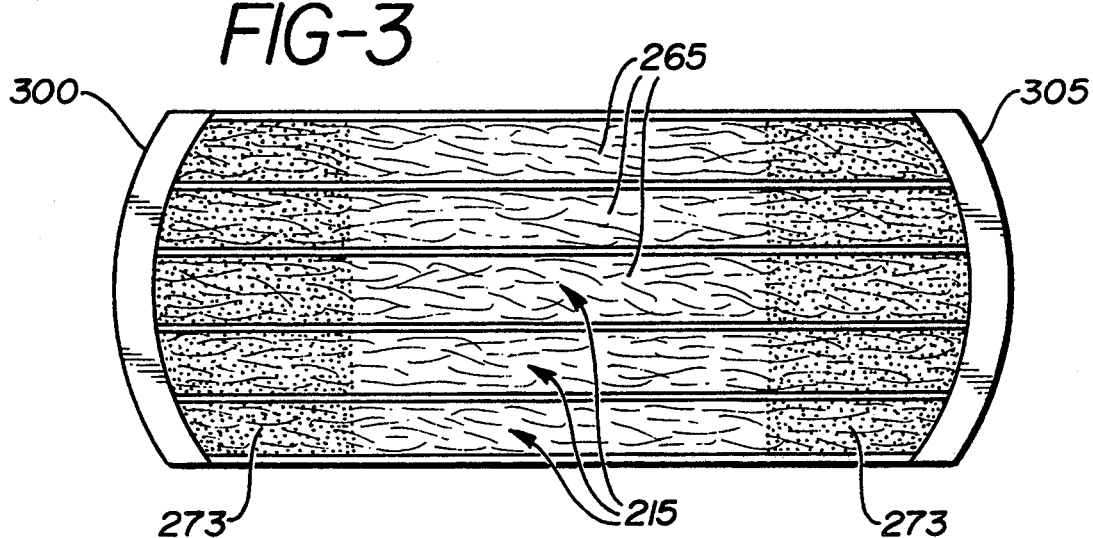
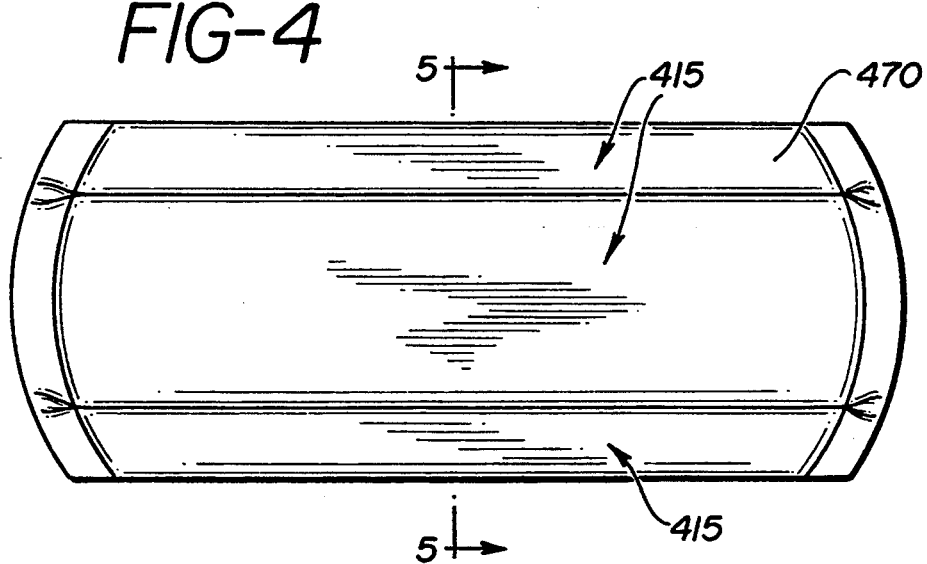
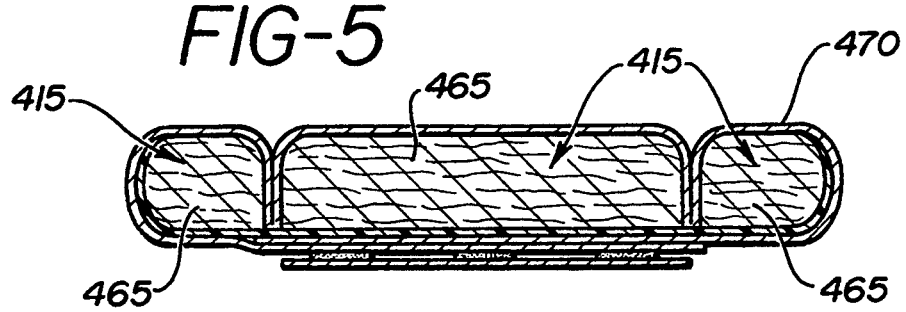

ABSORBENT STRUCTURE HAVING MULTIPLE CANALS

This is a continuation of application Ser. No. 07/916,921, filed Jul. 20, 1992, now abandoned, which is a divisional of Ser. No. 07/659,200, filed Feb. 21, 1991, now U.S. Pat. No. 5,151,091, which is a continuation of Ser. No. 07/247,820, filed Oct. 24, 1988, now abandoned.

BACKGROUND OF THE INVENTION

This invention relates to providing an article for absorbing body fluids. More particularly, this invention relates to an absorbent pad for use in products such as sanitary napkins, panty liners, diapers and the like.

In general, such products comprise one or more layers of a core of hydrophilic material such as wood pulp, rayon, tissue or the like. The hydrophilic material, generally fibrous in form, is provided as a pad having a rectangular or oblong shape or, in some cases, a shape designed to fit the anatomy of the wearer more closely. Such products may also be designed to have wings or flaps, which extend transversely from the product and serve to protect the wearer's panty from becoming stained due to the tendency for body fluid to flow over the sides of the napkin. The pad is usually provided with an enveloping cover pervious to body fluids on the side of the pad which is to be placed against the body and impervious to such fluids on the side facing away from the body. The object of such a body fluid impervious cover is, of course, to protect the wearer's clothing from staining and wetting.

In general, such products have satisfactorily performed their function of absorbing and retaining body fluids and preventing staining and wetting of the wearer's clothing. When the product is properly placed and retained by the wearer in its intended position, bodyfluid is directed at or near the center of the product and distributes, by means of liquid wicking, radially from the point of deposition throughout the absorbent medium. However, sometimes the product is misplaced, or becomes saturated with use. Further, the width of the product is generally much smaller compared to the length of the product. After striking the surface of the product, the fluid radiates approximately equally in all directions from the point of deposition. Thus, it tends to strike the longitudinal sides of the product before it travels toward the ends of the product, potentially causing staining at the sides before the full absorbent capacity of the product is utilized.

Sometimes, body fluid strikes the pad off-center and closer to the peripheral edges of the pad. If the body fluid strikes the pad off-center, the fluid tends to wick toward the side closest to which the fluids struck the pad and cause a failure, i.e., the staining and wetting of the clothing of the wearer by body fluid. Such failures are known as "side failures".

There have been efforts in the past to direct the flow of fluid in a longitudinal direction in order to provide means to saturate the napkin longitudinally, rather than laterally. For example, U.S. Pat. No. 4,524,474 (Svensson) describes an absorption pad for protecting a bed which includes a lower liquid impervious material layer and an upper liquid absorbent material layer laminated to the lower layer. The liquid absorbent layer is impregnated with strings or filaments of a liquid-resistant agent which does not stiffen the pad. The strings form a grid-like pattern for defining compartments between the strings over the entire area of the absorption pad. However, a grid-like pattern would not be effective in a sanitary napkin or like product because such a pattern would not effect a longitudinal saturation without aiding a lateral saturation. Furthermore, strings or filaments would not prevent excessive seepage throughout the absorbent material.

Canadian Patent No. 803,531 (Ruffo) describes a pad having a moisture-proof wrapper which is corrugated into a series of alternate, parallel ridges and grooves extending lengthwise of the napkin. This moisture-proof wrapper is placed beneath the absorbent layer and acts as a series of troughs to guide the body fluid along the longitudinal axis. However, this moisture-proof wrapper appears only at the bottom of a fibrous absorbent layer, thus allowing the body fluid to continue to flow along the transverse axis of the absorbent material and over the sides of the napkin.

U.S. Pat. No. 3,954,107 (Chesky et al.) describes an absorbent article having side portions which define a longitudinally extending channel adjacent the lateral midpoint of the pad, the side portions separating during use to expose an increased area of the pad assembly. However, this type of assembly may prove awkward during use, as it is designed to separate and fail to remain integrated. This pad is also likely to deform, which increases the probability of product failure.

It is, therefore, an object of this invention to provide an absorbent product capable of controlling and directing flow of body fluid so as to prevent failure at the sides and/or ends of the absorbent product.

Thus, it is an object of this invention to provide an absorbent product which is capable of directing body fluid to flow in longitudinal directions while substantially impeding the flow of such body fluid in transverse directions.

Another object of this invention is to provide an absorbent product which substantially prevents side failure.

It is yet another object of this invention to provide an absorbent product which may become largely saturated with body fluid without incurring side failure.

Another object of this invention is to provide a sanitary protection product which makes efficient use of the absorbent capacity of its absorbent element.

Yet another object of this invention is to provide a chambered sanitary protection product which substantially maintains its structural integrity during use.

SUMMARY OF THE INVENTION

In accordance with the principles of the present invention, an absorbent product is provided having means to direct fluid flow substantially along the longitudinal direction of the product and substantially limit or prevent side failure by substantially preventing the flow of fluid across the transverse axis of the product. In the absorbent product of this invention, two or more "canals", or chambers, are provided within an absorbent element which act to separate the absorbent element into a plurality of separate longitudinal absorbent areas along the longitudinal axis of the absorbent element.

The absorbent areas are separated by fluid repellent areas. These fluid repellent areas may be formed by the moisture barrier layer, which can be nipped or molded and formed into U-shaped canals. Alternatively, the fluid repellent areas may be formed of fluid repellent material such as fluid repellent fibers, fluid repellent fiber webs such as a nonwoven web of bicomponent fibers melt blown webs, repellent tissue, polymeric foams such as polyurethane or polymeric films arranged along the longitudinal axis of the absorbent element. The fluid repellent areas may include a relatively hydrophobic, or fluid repellent, cover or barrier material. Should a chamber become saturated with body fluid, the fluid will spill into the adjacent chamber.

Absorbent materials such as cellulose fiber, wood pulp, rayon, peat moss, pulp mixed with superabsorbent and the like may be placed in the canals to provide absorbent capacity. The absorbent element may be covered with a fibrous facing material, such as a non-woven fabric which aids in transmitting body fluid to the absorbent element. A clean, dry cover made of apertured polymeric film or repellent-treated fiber, which is hydrophobic and fluid permeable may also be used for this function. For example, an apertured film made in accordance with the teachings of U.S. Pat. No. 4,690,679 (Mattingly et al.) may be used. Preferably, a hydrophilic, or wetting nonwoven layer of material may be bonded to such clean and dry cover in order to improve said cover's wicking capacity.

BRIEF DESCRIPTION OF THE DRAWINGS

FIG. 3 is a plan view of another embodiment of the sanitary napkin of the current invention with the cover sheet removed to expose the absorbent material.

FIG. 4 is a plan view of another embodiment of the sanitary napkin of the current invention having three chambers.

FIG. 5 is a cross-section through line 5—5 shown in FIG. 4.

DETAILED DESCRIPTION OF THE PREFERRED EMBODIMENTS

Figure 1:
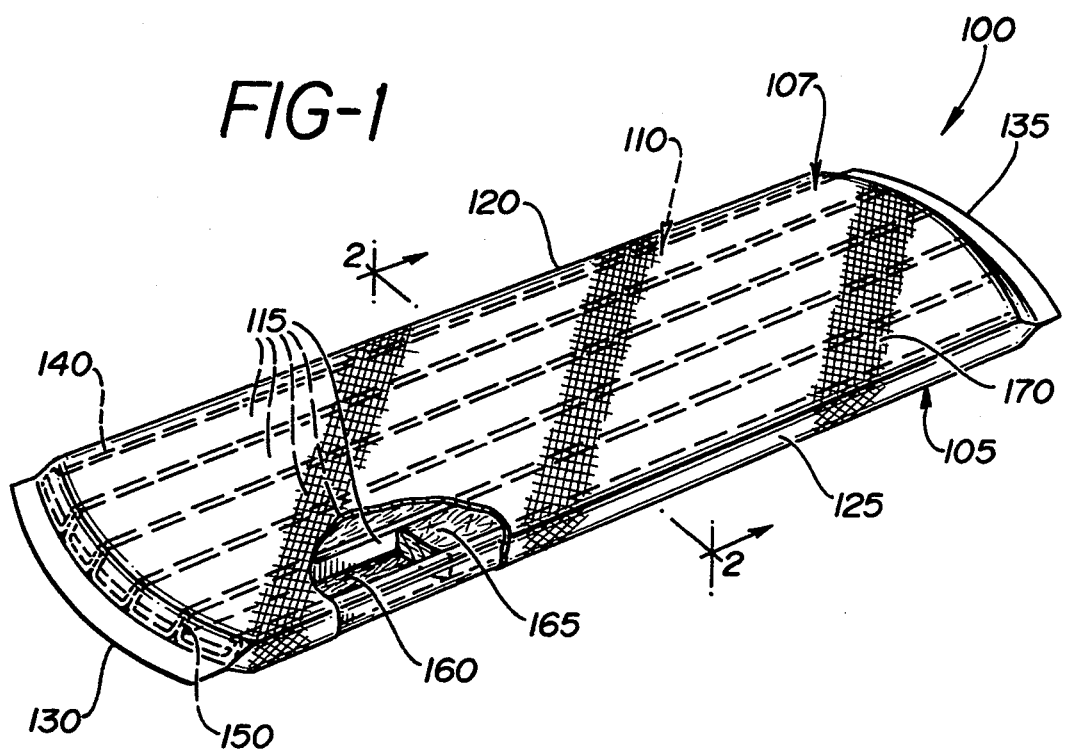
FIG. 1 depicts a perspective view of a sanitary napkin according to the current invention with the cover sheet partially removed to expose the plurality of chambers.

FIG. 1 depicts a cross-sectional view of a sanitary napkin 100 made in accordance with the principles of this invention. Sanitary napkin 100 is provided with a centrally located absorbent element 110 having generally longitudinally extending edges 120 and 125 and transversely extending ends 130 and 135. Sanitary napkin 100 has a garment-facing side 105 and a body-facing side 107. Absorbent element 110 is composed of a plurality of chambers 115 extending along the longitudinal axis of the napkin. Chambers 115 are formed by fluid repellent barrier 140.

Figure 2:
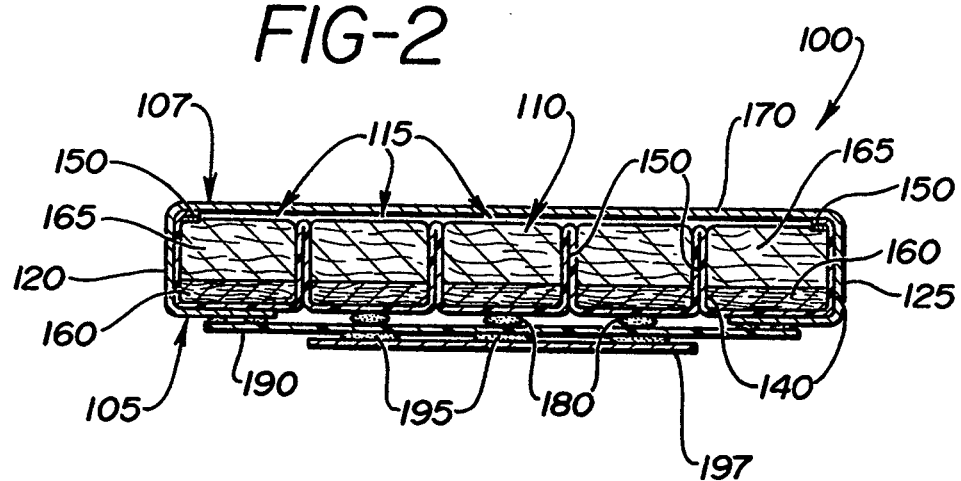
FIG. 2 is a cross-section through line 2—2 shown in FIG. 1.

Fluid repellent barrier 140 may be formed into said chamber-separation means by adhering the barrier into position with binder adhesive 150 between verticalspaces and then nipping repellent barrier 140. Repellent barrier 140 so as to create folds in the barrier that form walls that extend along the entirety of the length of the absorbent element 110, as shown in FIGS. 1 and 2 may be made of any polymeric film such as polyethylene, polypropylene, polyurethane or cellophane or may be made from nonwoven moisture impermeable fibers, or may be a normally fluid pervious material that has been treated to be impervious, such as a fluid repellent paper or silicone-treated paper, repellent-treated-fabrics, coated tissues such as silicone-coated cellulose tissue, superabsorbent carriers, microporous films or apertured polymeric films. The barrier may also be made of fiber webs containing fluid repellent fiber such as polyester, rayon, or acrylic fibers.

In one preferred embodiment, the repellent barrier may be a coextruded polyethylene/ethyl, vinyl-acetate copolymer film (PE/EVA). This film may be heated to activate the EVA and then nipped with the EVA side facing toward the garment facing side of the napkin. The structure will adhere in the nipped shape, thus forming chambers without the use of adhesive. Binder adhesive 150 is also applied to the body facing surface 107 of repellent barrier in order to contact and adhere to absorbent material placed in the chambers.

Materials other than polymeric film barriers and repellent non-woven facings may be used to create chambers in the absorbent products of this invention. For example, an insert strip of bonded 0.8 oz/yd$^2$ Hollofil* (*a Trademark of E. I. du Pont de Nemours) hollow fibers may be placed between the chambers. Fluid transfer is then controlled by the density and thickness of the Hollofil* inserts. On the garment facing side of the absorbent element in such an embodiment, there should be located a moisture-proof barrier. Other materials useful as fluid repellant barriers include open cell foams (e.g. polyurethane), closed cell foams and microporous films.

Fluid repellant barrier 140 may be formed into a U-shaped middle chamber and one or more additional barriers may be added which are formed into larger U-shapes which are nested concentrically and arranged such that additional chambers are formed between the arms of the "U's". In such a configuration, the largest "U" forms an impervious barrier on the undergarment-facing side of the pad.

Binder adhesive 150 may be any of a large number of pressure-sensitive tack hot melt adhesives, thermosetting adhesives, cold glue adhesives or the like that are commercially available, including styrene/ethylene/-butylene/styrene (SEBS) block terpolymers, styrene-isoprene-styrene copolymers and the like. Examples of hot melt adhesives useful as binder adhesives in the products of this invention are: Fuller HM-3350-C, available from the H. B. Fuller Co., hot melt adhesive containing amorphous polypropylene and hydrocarbon tackifiers (viscosity 3800±950 cps at 300° F., density 0.88 g ice at 70° F., softening range 1950°±20° F., applicator temperature 275° F. to 325° F.). Eastobond A3375S (available from Eastman Chemical Products, Inc.), having an amorphous polypropylene base coated with polyethylene to facilitate handling (viscosity 1500±400 cps at 350° F., density 0.90±0.01 g/cc at 73° F., softening range 208° F.±12° F.-30° F. and applicator temperature 275°-325° F.); National Starch 5432-119-1 (available from National Starch & Chemical Corp.), having a viscosity of 2135 cps at 300° F., a softening point of 139° F. and an applicator temperature of 250°-350° F.; and the like. Cold glue polyvinyl acetate-based adhesives are also useful. Binder adhesive may be applied in the form of longitudinal lines, sprays, spots, squares, transverse lines or any other suitable pattern.

High density absorbent material 160 may be placed at the bottom of each chamber 115 in order to provide a reservoir for holding absorbed body fluid. High density absorbent material 160 which may contain superabsorbent or peat moss or like material to aid in absorbing may be a densified wood pulp board, a densified pulp-polyethylene mixture, highly absorbent tissue impregnated with superabsorbent, cardboard or pulp fluff board which has been crushed to make it more flexible; a densified, compacted, porous, absorbent, fibrous layer having a particulate hydrocolloid material, such as starch grafted polyacrylate powder, distributed therein such as described in U.S. Pat. No. 4,217,901, issued Aug. 19, 1980 (Bradstreet et al.) or the like. Low density absorbent material 165 such as cellulose fibers, wood pulp, pulp/polyester mixtures or the like is placed in each chamber 115 closer to the body facing side 107 of the napkin in order to wick body fluid away from the surface of the napkin.

Low density absorbent material 165 may be low density loosely associated cellulose fibers, e.g. wood pulp fluff, regenerated cellulose, cotton fibers or bicomponent fusible fibers having an outer core which melts at relatively lower temperatures and an inner core which melts at higher temperatures. Such fibers may be chemically or physically modified and the absorbent element may include such fibers in combination with other materials, both natural and synthetic, such as hydrophilic foams, hydrophilic polymers or the like. Wood pulp is frequently the material of choice primarily because it is inexpensive and readily available.

Figure 6:
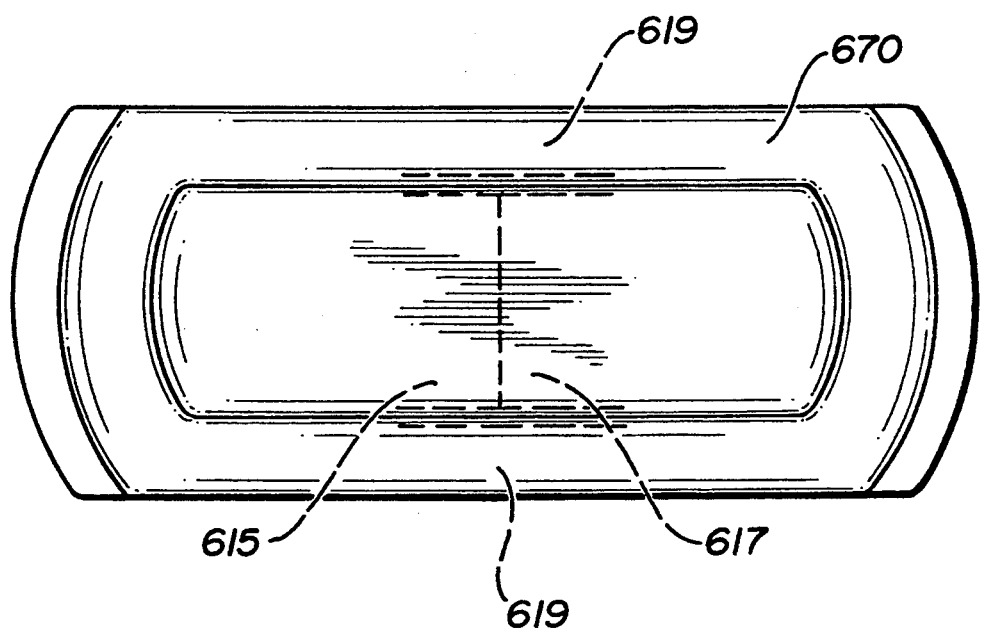
FIG. 6 is a plan view of another embodiment of the sanitary napkin of the current invention having chambers separated by the cover.

Cover 170 surrounds absorbent element on the body facing side of the napkin and wraps around the longitudinal edges of the absorbent element and partially under the repellent barrier. Alternatively, cover 170 may surround the entire absorbent element so as to completely encase it. Cover 170 may also be folded between the chambers to form barriers, as shown in FIG. 6. Cover 170 may be any of the well known cover materials used in sanitary protection products, including, for example, nonwoven fabrics of cellulose, regenerated cellulose, polyester or other synthetic polymers. Additionally, polymeric film or films having apertures therethrough to render the materials pervious to fluids may also be employed. One cover material of choice is a fabric containing a blend of pulp and fusible fibers such as heat bondable polyester/polyethylene conjugate fibers.

Laminating adhesive 180, which may be a hot melt adhesive, is placed along longitudinal lines under the repellent barrier and cover fabric to adhere the repellent barrier and cover fabric to a moisture-impermeable barrier 190. Alternatively, a non-woven cover fabric may be wrapped around the entire absorbent structure to maintain its integrity without the need for an additional barrier 190. Barrier 190 may be polyethylene or similar polymeric moisture-resistant material or a nonwoven fabric which has been treated to render it moisture-impermeable.

Positioning adhesive 195 is placed along longitudinal lines or in any suitable pattern on the garment facing side of the absorbent body to aid in positioning the absorbent body on an undergarment. Positioning adhesive 195 may be a pressure sensitive hot melt adhesive. Release paper 197 protects the positioning adhesive 195 prior to use by the wearer.

Longitudinal chamber walls 115 may be spaced from between about ⅛ inch apart to about 2 inches apart. Most preferably they are about ½ inch apart. In other embodiments, there may be a relatively wide chamber located in the center of the napkin and narrower chambers on either side of the central chamber. The width between chamber walls may be exactly the same as the width between other chamber walls along the transverse axis of the napkin or it may be varied with respect to the width of other canals. Of course, the chambers need not be linear, but may be arranged in any pattern conducive to achieving the generally longitudinal flow of fluid in the product.

In another embodiment, a controlled release of fluid from the center of the absorbent may be achieved by placing absorbent material having successively greater hydrophobicity, or fluid repellancy, in the chambers adjacent the central chambers.

The surface of the chamber separation means closest to the body facing surface of the napkin should effect a segmentation of the absorbent material of the napkin. This discourages fluid transfer between canals along the transverse axis of the napkin. Thus, fluid is encouraged to flow along the longitudinal axis of the absorbent material without spilling over or transferring into adjacent canals.

FIG. 3 depicts another preferred embodiment of the absorbent products of this invention. In FIG. 3, the cover material has been removed to permit the viewing of an absorbent element containing low density absorbent material 265 in the central portion chambers 215. Located in chambers 215 toward longitudinal ends 300 and 305 is superabsorbent material 273 which may be composed of low density absorbent material with natural or manufactured superabsorbent such as peat moss, polymeric material or the like.

FIGS. 4 and 5 depict another preferred embodiment of this invention. The sanitary napkin depicted in FIG. 4 contains three chambers 415. These chambers are separated by a cover 470. Chambers 415 are filled with low density absorbent material 465. Cover 470 is more fluid repellant than low density absorbent material 465. Cover 470 may be made of any material known to be useful in sanitary protection products. For example, nonwoven fabrics which have been treated to render them relatively hydrophobic in comparison with the low density absorbent material may be used, as well as synthetic polymer films having apertures. As long as the cover is less hydrophilic than the absorbent material, the fluid is more apt to wick along the absorbent. When saturated, the cover wall allows controlled release of fluid to the next chamber. The release action from chamber to chamber is controlled by the difference in hydrophobicity between the absorbent and the wall, and by the thickness of the wall. Cover 470 completely surrounds the absorbent element and keeps it unified.

FIG. 6 depicts another preferred embodiment of the products of this invention. Chambers 615, 617 and 619 are separated by cover 670 in a manner similar to that of FIG. 5. Fluid striking the napkin will tend to fill chambers 615 and 617 before radiating to chamber 619, which surrounds chambers 615 and 617. Chamber 619 may contain absorbent material which is slightly more fluid-repellent than that of chambers 615 and 617. Alternatively, chambers 615 and 617 may be combined into one chamber. This construction would discourage the fluid from migrating to chamber 619, which is adjacent to the body and undergarments of the wearer. Alternatively, chamber 619 may contain low density absorbent material and superabsorbent, which would tend to prevent the fluid from leaking out of the napkin.

In an alternative embodiment, chambers 615, 617 and 619 may be separated by an impermeable barrier layer below the absorbent element, or by a relatively hydrophobic barrier wall formed by the following examples illustrate the concepts and products of this invention. However, they merely serve to illustrate and not to limit the scope of the invention.

EXAMPLE 1

Three experimental multiple canal sanitary napkin products were fabricated in accordance with the teachings of this invention. Control napkins, commercially available as SURE & NATURAL brand sanitary napkins, were tested in addition to napkins made according to this invention. A first experimental product (A) was fabricated with four canals which were 0.625 inches apart. Experimental product (B) was fabricated with five canals which were 0.500 inches apart. Experimental product (C) was made with eight canals each of which was 0.3125 inches wide. The control product consisted of a 2.5 inch wide absorbent structure having a polyethylene boat enwrapping the absorbent pad.

A test apparatus was used to analyze all of the sanitary napkin products. This consisted of a fast dynamic fluid capacity analyzer was used to measure the absorbency performance of sanitary napkin products in a simulation to in vivo usage conditions. Each of the sample napkins was suspended across a rubber mold which simulates the female form. The form was set into motion by means of a set of gears, cams, and rods and an ersatz menstrual fluid containing 1% sodium chloride, by weight, was allowed to drip onto the napkin to simulate in-use conditions. The fluid was applied at a rate of 15.2 cc/cycle and the form was operated at a speed of 1.0 cycles/minute. The fluid capacity of the napkin under dynamic conditions was measured by the total volume of fluid applied at the time of failure, i.e., the time at which the spotting was noted on the underside of the napkin. The fluid was dispensed to the sanitary napkin product at approximately a 90° angle to the body facing surface of the pads until failure occurred at the sides of the product.

The results of this dynamic laboratory test are shown in Table I below. The data in Table I demonstrate a cubic centimeters of ersatz menstrual fluid which was contained in each pad prior to failure. The experimental 0.625 inch canals had an 11% absorbency increase over the control product. The 0.5 inch canals had a 33% absorbency increase over the control product. The 0.3125 inch canals had a 22% absorbency increase over the control samples. The data shows that the most preferable spacing for a 2.5 inch width product is 0.5 inches between canals.

EXAMPLE 2

Sanitary napkin products containing three longitudinal chambers were fabricated in accordance with the teachings of this invention. The middle chamber contained low density wood pulp and polyester binder fiber. The side chambers were made from fused Hollofil fibers rolled along the longitudinal direction and coated with polyacrylic acid superabsorbent. The cover was an apertured fiber cover sprayed on the product-facing side for adhesion to the absorbent element.

These products were tested to observe absorbency using ten panelists. Each panelist used the tri-chambered napkins during one month and STAYFREE brand Maxipads the following month. The pads were worn for five hours or until failure. The results of this test are set forth in Table II. The results show that the chambered napkins significantly reduced the rate of failure as compared to the non-chambered napkins.

EXAMPLE 3

Sanitary napkin products were fabricated in accordance with the teachings of this invention containing three longitudinal chambers filled with low density wood pulp and polyester binder fiber. Nonwoven cover material made from polyester and rayon was used to form chamber walls dividing the chambers. The cover was more fluid repellent than the pulp. The middle chamber of each absorbent was about 1½ inches across the transverse width. The chambers on either side of the middle chamber were about ½ inch in width. Eleven women were asked to wear the chambered napkins during their menstrual periods, in the days of the heaviest flow for a period of 5 hours, or until failure. The following month, the same eleven women were asked to wear STAYFREE brand maxipads under the same conditions to provide a comparison. The results of these tests are set forth in Table III. The results of these tests show that the frequency of daytime failures was diminished when the chambered napkins were used. In addition, the chambered napkins of this invention produced less severe stains on panties when failure occurred.

EXAMPLE 4

The 0.500" chambered napkin of Example 1 was tested as in Example 3. The results of this test are set forth in Table IV. Both the SURE AND NATURAL brand napkins and the chambered napkins of this invention evidenced a failure rate higher than 40% under the conditions of the test. Due to the light flow rate of the women tested (0.75 g/hr. and 0.09 gl/hr), the menstrual fluid apparently wicked along the cover of the napkins and did not reach the absorbent element of the pads. The stains produced were predominantly "light smears", indicative of failures caused by cover wicking, rather than by lack of absorbent capacity.

TABLE I

PRODUCT DYNAMIC CAPACITY PRIOR TO FAILURE (cc/PAD)

| Test No. | Control | Chamber Width | | |
|---|---|---|---|---|
| | | 0.625" | 0.500" | 0.3125" |
| 1 | 30.41 | 22.95 | 40.20 | 31.31 |
| 2 | 24.86 | 23.57 | 39.61 | 31.30 |
| 3 | 21.71 | 20.99 | 29.58 | 30.20 |
| 4 | 31.35 | 31.85 | 36.10 | 27.63 |
| 5 | 23.78 | 29.62 | 26.51 | 33.08 |
| 6 | 22.26 | 27.82 | 39.95 | |
| 7 | 22.02 | 26.15 | 29.00 | |
| 8 | 22.55 | 35.23 | 25.16 | |
| 9 | 23.37 | 28.48 | 24.98 | |
| 10 | 29.15 | 31.48 | 42.25 | |
| Mean (x) | 25.15 | 27.81 | 33.33 | 30.70 |

TABLE II

| | Chambered Napkins | STAYFREE brand Maxipads |
|---|---|---|
| Total Daytime Napkins | 77 | 89 |
| Average add-on wgt. (g) | 7.35 | 7.98 |
| Average time worn (hours) | 4.50 | 4.42 |
| Average flow rate (g/hr.) | 1.76 | 2.32 |
| Daytime Failures | 34 (44%) | 51 (57%) |
| Avg. failure capacity (g) | 7.83 | 10.34 |
| Avg. time worn at failure (hours) | 4.23 | 4.29 |
| No. of failures | | |
| ≦2 g | 5 | 5 |
| ≦6 g | 17 | 14 |
| ≦12 g | 28 | 36 |
| No. of failures | | |

TABLE II-continued

|  | Chambered Napkins | STAYFREE brand Maxipads |
|---|---|---|
| ≦1 hr. | 0 | 0 |
| ≦2 hrs. | 1 | 4 |
| ≦3 hrs. | 1 | 8 |
| ≦4 hrs. | 5 | 19 |
| ≦5 hrs. | 14 | 39 |
| Failure type |  |  |
| Side Only | 19 | 21 |
| End Only | 14 | 16 |
| Combination (side and end) | 3 | 12 |
| Panelists with failures ≦4 hrs. | 6 | 8 |
| No. of panelists with reduced failure | 7 | 4 |
| Stain Intensities |  |  |
| Light smear | 25 | 33 |
| Light stain | 3 | 11 |
| Moderate stain | 2 | 5 |

TABLE III

|  | STAYFREE Maxipads | Chambered Napkins |
|---|---|---|
| Total Daytime Napkins | 75 | 68 |
| Avg. add-on weight (g) | 6.15 | 7.23 |
| Avg. time worn (hrs.) | 4.33 | 4.61 |
| Avg. flow rate (g/hr.) | 1.68 | 1.94 |
| Daytime failures | 47 (62.67%) | 21 (30.88%) |
| Avg. time worn (hrs.) of failed napkin | 6.97 | 8.80 |
| Avg. failure capacity | 4.31 | 4.49 |
| No. of failures |  |  |
| ≦2 g. | 5 | 4 |
| ≦6 g. | 25 | 11 |
| ≦12 g. | 42 | 15 |
| No of failures |  |  |
| ≦1 hr. | 0 | 1 |
| ≦2 hrs. | 4 | 3 |
| ≦3 hrs. | 7 | 7 |
| ≦4 hrs. | 17 | 8 |
| ≦5 hrs. | 35 | 15 |
| Failure type |  |  |
| Side Only | 19 | 11 |
| End Only | 18 | 5 |
| Combination (Side & End) | 1 | 5 |
| Panelists with failures at ≦4 hrs. | 7 | 4 |
| No of panelists with reduced failure | 1 | 8 |
| Stain Intensities |  |  |
| Light Smear | 33 | 15 |
| Light Stain | 12 | 2 |
| Moderate Stain | 2 | 4 |

TABLE IV

|  | SURE & NATURAL | Chambered Napkins |
|---|---|---|
| Total Daytime Napkins | 39 | 39 |
| Avg. capacity (g) | 3.08 | 3.28 |
| Avg. time worn (hrs.) | 4.94 | 4.93 |
| Avg. flow rate (g/hr.) | 0.75 | 0.90 |
| Daytime Failures | 16 (41.0%) | 19 (48.7%) |
| Avg. failure capacity | 3.18 | 3.87 |
| No. of failures |  |  |
| ≦2 g. | 4 | 8 |
| ≦4 g. | 8 | 3 |
| ≦8 g. | 3 | 7 |
| ≦12 g. | 1 | 1 |
| No of failures |  |  |
| ≦2 hr. | 4 | 3 |
| ≦4 hrs. | 5 | 5 |
| ≦6 hrs. | 5 | 11 |
| ≦6 hrs. | 2 | 0 |
| Failure type |  |  |

TABLE IV-continued

|  | SURE & NATURAL | Chambered Napkins |
|---|---|---|
| Side Only | 10 | 8 |
| End Only | 2 | 3 |
| Combination (Side & End) | 4 | 8 |
| Panelists with failures at ≦4 hrs. | 12 | 11 |
| Stain Intensities |  |  |
| Light Smear | 14 | 14 |
| Light Stain | 2 | 5 |
| Moderate Stain | 0 | 0 |

What is claimed is:

1. An absorbent product comprising:
   a) an absorbent core having longitudinally extending sides, transverse ends, a body-facing side and a garment-facing side, said transverse ends defining an absorbent core length therebetween;
   b) a fluid permeable cover on said body-facing side; and
   c) a plurality of absorbent chambers formed by fluid impermeable walls extending longitudinally within said absorbent core, said fluid impermeable walls preventing fluid communication between said chambers, said chambers containing absorbent material such that the absorbent material in each of said chambers is isolated from the absorbent material in adjacent chambers.

2. An absorbent product according to claim 1 wherein said fluid impermeable walls are formed from a material selected from the group consisting of moisture impermeable polymeric film and polymeric foam.

3. An absorbent structure according to claim 2 wherein said impermeable polymeric film is selected from the group consisting of polyethylene, polypropylene, polyurethane, and cellophane.

4. An absorbent product according to claim 2 wherein said polymeric foam comprises polyurethane.

5. An absorbent product according to claim 1 wherein said absorbent material comprises wood pulp fluff, regenerated cellulose, cotton fibers, peat moss or a combination thereof.

6. An absorbent product according to claim 1 wherein said absorbent material comprises high density absorbent located adjacent the garment-facing side of the absorbent structure and low density absorbent adjacent the body-facing side of the absorbent structure.

7. An absorbent product according to claim 6 wherein said high density absorbent comprises wood pulp fluff and superabsorbent.

8. An absorbent product according to claim 7 wherein said superabsorbent comprises a starch grafted polyacrylate powder.

9. An absorbent product according to claim 6 wherein said low density absorbent comprises wood pulp fluff, regenerated cellulose, rayon, cotton or a combination thereof.

10. An absorbent product according to claim 1, wherein said fluid controlling walls are as long as said absorbent core.

11. An absorbent product according to claim 1, further comprising a fluid impermeable barrier on said garment facing side, and wherein said fluid impermeable walls are formed by said fluid impermeable barrier.

12. An absorbent product according to claim 11, wherein said fluid impermeable walls are formed by folds formed in said fluid impermeable barrier between each of said absorbent chambers.

13. An absorbent product according to claim 1, wherein each of said chambers has a transverse width of approximately 0.5 inch.

14. An absorbent article having longitudinally extending sides, first and second transverse ends, a body facing surface and a garment facing surface, comprising:
 a) a fluid permeable cover disposed on said body facing surface;
 b) a fluid repellant barrier disposed on said garment facing surface;
 c) a plurality of longitudinally extending chambers, each of said chambers separated by fluid controlling walls;
 d) a first absorbent material disposed longitudinally in a central portion of each of said chambers; and
 e) first and second fluid reservoirs for each of said chambers formed by a second absorbent material, each of said first fluid reservoirs disposed in its respective chamber between said first absorbent material and said first transverse end, each of said second fluid reservoirs disposed in its respective chamber between said first absorbent material and second transverse end, said first absorbent material having a lower density than said second absorbent material, whereby said first absorbent material wicks fluid longitudinally away from said central portion of each of said chambers to said fluid reservoirs.

15. An absorbent article according to claim 14, wherein said first absorbent material comprises cellulose fibers and said second absorbent material comprises a superabsorbent.

16. An absorbent product according to claim 14 wherein said fluid controlling walls are formed from a material selected from the group consisting of nonwoven moisture impermeable fiber, moisture impermeable polymeric film, a repellent-treated fabric, repellent-treated tissue, moisture repellent fiber web, superabsorbent barrier or polymeric foam.

17. An absorbent article having first and second longitudinally extending sides, transverse ends, a body facing surface and a garment facing surface, comprising:
 a) a fluid permeable cover disposed on said body facing surface;
 b) a fluid repellant barrier disposed on said garment facing surface;
 c) first, second and third longitudinally extending chambers, said first and second chambers separated by a first fluid controlling wall, said first and third chambers separated by a second fluid controlling wall, said first chamber being approximately centrally disposed between said first and second longitudinal sides, said second chamber being disposed between said first chamber and said first longitudinal side, said third chamber being disposed between said first chamber and said second longitudinal side; and
 d) first, second and third adsorbents disposed in said first, second and third chambers, respectively, said second and third adsorbents each having greater hydrophobicity than said first absorbent.

18. An absorbent article according to claim 17, further comprising:
 a) fourth and fifth longitudinally extending chambers, each of said chambers separated by fluid controlling walls, said fourth chamber being separated from said second chamber by a third fluid controlling wall and disposed between said second chamber and said first longitudinal side, said fifth chamber being separated from said third chamber by a fourth fluid controlling wall and disposed between said third chamber and said second longitudinal side; and
 d) fourth and fifth adsorbents disposed in said fourth and fifth chambers, respectively, said fourth absorbent having greater hydrophobicity than said second absorbent, said fifth absorbent having greater hydrophobicity than said third absorbent.

19. An absorbent product according to claim 17 wherein said first and second fluid controlling walls are formed from a material selected from the group consisting of nonwoven moisture impermeable fiber, moisture impermeable polymeric film, a repellent-treated fabric, repellent-treated tissue, moisture repellent fiber web, superabsorbent barrier and polymeric foam.

20. An absorbent article having first and second longitudinally extending sides, first and second transverse ends, a body facing surface and a garment facing surface, comprising:
 a) a fluid permeable cover disposed on said garment facing surface;
 b) a fluid repellant barrier disposed on said garment facing surface;
 c) a first absorbent disposed in a portion of said article that is centrally disposed between said first and second longitudinal sides and between said first and second transverse ends;
 d) a second absorbent surrounding said first absorbent wherein said second absorbent is more fluid repellant than said first absorbent; and
 e) a first fluid controlling wall separating said first and second absorbents.

21. An absorbent article according to claim 20, wherein said second absorbent comprises a superabsorbent.

22. An absorbent article according to claim 20, further comprising a second fluid controlling wall extending transversely through said first absorbent so as divide said first absorbent into first and second portions.

23. An absorbent product according to claim 20 wherein said first and second fluid controlling walls are formed from a material selected from the group consisting of nonwoven moisture impermeable fiber, moisture impermeable polymeric film, a repellent-treated fabric, repellent-treated tissue, moisture repellent fiber web, superabsorbent barrier or polymeric foam.

* * * * *